United States Patent [19]

Ashwood et al.

[11] Patent Number: 5,310,899

[45] Date of Patent: May 10, 1994

[54] PROCESS FOR THE PREPARATION OF CHIRAL 4-ARYLOXYAZETIDINONES

[75] Inventors: Michael S. Ashwood; Brian C. Bishop, both of Bishops Stortford; Peter G. Houghton, Bassingbourn, all of England; Guy R. Humphrey, Bell Mead, N.J.

[73] Assignee: Merck Sharpe & Dohme Ltd., Hertfordshire

[21] Appl. No.: 20,518

[22] Filed: Feb. 22, 1993

Related U.S. Application Data

[63] Continuation of Ser. No. 839,989, Feb. 20, 1992, abandoned.

[30] Foreign Application Priority Data

Feb. 21, 1991 [GB] United Kingdom ............... 9103654

[51] Int. Cl.$^5$ ............... C07B 53/00; C07B 55/00; C07D 205/08
[52] U.S. Cl. ............................................. 540/360
[58] Field of Search ................................. 540/360

[56] References Cited

FOREIGN PATENT DOCUMENTS 0199630 10/1980 European Pat. Off. .
0259268 3/1988 European Pat. Off. .
0337549 10/1989 European Pat. Off. .
0481671 4/1992 European Pat. Off. .

OTHER PUBLICATIONS

Chem. Rev., vol. 76 (1976) Russmussor et al.
Justus Liebigs Ann. Chem., 1974, 539, by Claus, et al.
10th Coll. Chem. Comps. Index, pp. 7086CS–7088CS (1985) (Cumulative).
Sunagawa, Chem Abs 104, 207051 (1986).
J.C.S. Chem. Commun., pp. 1324–1325 (1982), by Shibasaki, et al.
Chem. Absts., vol. 101, 72522Y by Takeda (1984).
Ikagami Chem. Abst., vol. 104, 33947h (1986).
Tetrahedron Letters, No. 52, 1979, G. B. pp. 5063–5066, by D. Boucherot, et al.

*Primary Examiner*—Mark L. Berch
*Attorney, Agent, or Firm*—Robert J. North; Melvin Winokur

[57] ABSTRACT

A process for preparing a single enantiomer of a 4-aryloxyazetidin-2-one derivative in optically pure form comprises reacting a hindered vinyl ester with chlorosulphonyl isocyanate; displacing the hindered acyloxy group with a phenolic derivative containing a protected carboxy group; deprotecting the carboxylate moiety; resolving with a chiral amine; filtering; and regenerating the desired enantiomer by acidification. A method for enriching the product obtained from the acyloxy displacement step in favour of the desired enantiomeric form, by treating with an asymmetric catalyst such as a chiral alkaloid derivative, is provided; as also is a method for racemising the unwanted antipode of the desired 4-aryloxyazetidin-2-one enantiomer. The invention further provides novel enantiomers based on the 4-aryloxyazetidin-2-one ring structure.

6 Claims, No Drawings

PROCESS FOR THE PREPARATION OF CHIRAL 4-ARYLOXYAZETIDINONES

This is a continuation of U.S. patent application Ser. No. 07/839,989, filed Feb. 20, 1992.

The present invention relates to the preparation of an optically-pure compound. More particularly, the invention concerns an improved process for producing the desired enantiomer of a 4-aryloxyazetidin-2-one derivative in optically-pure form.

EP-A-0199630 and EP-A-0337549 describe various types of N-substituted 4-aryloxyazetidin-2-ones which are potent elastase inhibitors and are therefore useful as anti-inflammatory and antidegenerative agents. These publications illustrate various methods for preparing the active compounds, one such method involving attachment of the N-substituent to a 4-aryloxyazetidin-2-one precursor wherein the nitrogen atom in the azetidinone ring is unsubstituted. The 4-aryloxyazetidin-2-one precursor is prepared by reaction of an optionally substituted phenol with an appropriate 4-acetoxyazetidin-2-one derivative, which in turn is prepared by cycloaddition of chlorosulphonyl isocyanate with the corresponding enol acetyl ester.

The scope of the chlorosulphonyl isocyanate cycloaddition reaction with alkenes has been extensively reviewed in. *Chem. Rev.*, 1976, 76. 389. In particular, the preparation of 4-acyloxyazetidin-2-ones from the cycloaddition reaction between chlorosulphonyl isocyanate and various vinyl esters is described in some detail in *Justus Liebigs Ann. Chem.*, 1974, 539. A significant drawback encountered with the reaction between chlorosulphonyl isocyanate and vinyl acetate derivatives, however, is that the yields obtained tend to be moderate at best (of the order of 40%); and the resulting 4-acetoxyazetidin-2-one intermediates are generally unstable, thereby giving rise to appreciable problems in handling.

The acetoxy group is displaced from the 4-acetoxyazetidin-2-one intermediate using an optionally substituted phenol derivative to give the 4-aryloxyazetidin-2-one precursor to the desired active N-substituted 4-aryloxyazetidin-2-one product. Since the 4-acetoxyazetidin-2-one intermediate is racemic, it follows that the product obtained from this displacement reaction is also racemic. In order to achieve maximum therapeutic utility for the final product, it is clearly desirable to administer, and thus produce, the single enantiomer of this product in which the majority of activity resides. From a synthetic viewpoint, it is preferable to perform the resolution as early as possible in the synthetic sequence. Thus, a suitable candidate for resolution is the 4-aryloxyazetidin-2-one precursor wherein the nitrogen atom in the azetidinone ring is unsubstituted. Attempts have therefore been made in the past to influence the stereochemical outcome of the acetoxy displacement reaction, for example by performing the reaction in the presence of a base such as sodium carbonate, together with a catalytic quantity of cinchonine. The most favourable results obtained from this reaction to date, however, have been a 70:30 mixture of enantiomers in approximately 70% yield. A notable drawback with this approach concerns the need for chromatography of the product in order to remove residual phenolic starting material, which represents a clear obstacle to adaptation of the process for operation on an industrial scale.

It will be apparent from the above discussion that there are various drawbacks associated with existing methods for preparing chiral 4-aryloxyazetidin-2-ones. The present invention accordingly provides an improved process for preparing this class of compounds which overcomes these disadvantages.

According to one feature of the present invention, there is provided a process for the preparation of a single enantiomer of a 4-aryloxyazetidin-2-one derivative of formula I:

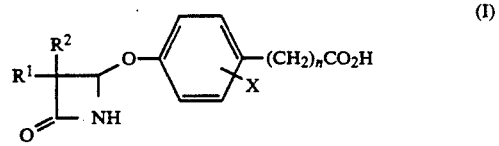

wherein n is zero or a positive whole integer from 1 to 6; $R^1$ and $R^2$ independently represent hydrogen, $C_{1-6}$ alkyl or $C_{1-6}$ alkoxy($C_{1-6}$)alkyl; and X represents hydrogen, halogen, $C_{1-6}$ alkyl or $C_{1-6}$ alkoxy; which process comprises the following steps:

(i) reaction of a compound of formula II:

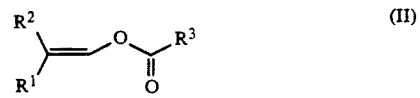

wherein $R^1$ and $R^2$ are as defined above, and $R^3$ represents a hindered acyl residue; with chlorosulphonyl isocyanate, to obtain a β-lactam derivative of formula III:

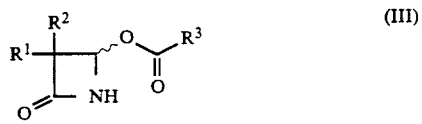

wherein $R^1$, $R^2$ and $R^3$ are as defined above, and the wavy line indicates that a mixture of enantiomers at the position indicated is obtained;

(ii) reaction of the β-lactam derivative of formula III thereby obtained with a phenolic compound of formula IV:

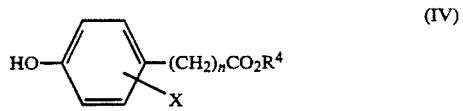

wherein n and X are as defined above, and $R^4$ represents a carboxy-protecting group; in the presence of a base, to obtain a compound of formula V:

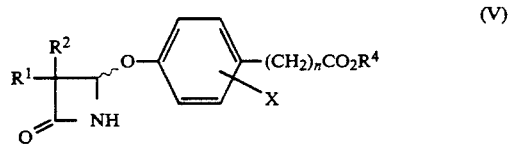

wherein n, $R^1$, $R^2$, $R^4$, X and the wavy line are as defined above;

(iii) removal of the carboxy-protecting group $R^4$ from the compound of formula V thereby obtained, to obtain a compound of formula IA:

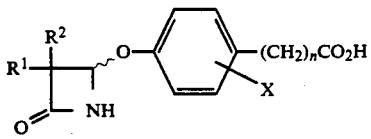

(IA)

wherein n, $R^1$, $R^2$, X and the wavy line are as defined above;

(iv) treatment of the compound of formula IA thereby obtained with an approximately equimolar amount of an appropriate chiral amine, to obtain the corresponding chiral amine salt of the desired enantiomer of the β-lactam carboxylic acid of formula I;

(v) filtering the reaction mixture; and (vi) acidifying the solid salt thereby obtained in order to regenerate the desired enantiomer of the 4-aryloxyazetidin-2-one derivative of formula I in substantially optically-pure form.

Particular values of n in formula I above are zero, 1, 2 and 3. Preferably, n is 1.

The groups $R^1$ and $R^2$ in the compounds of formula I above independently represent hydrogen, $C_{1-6}$ alkyl or $C_{1-6}$ alkoxy($C_{1-6}$)alkyl. The $C_{1-6}$ alkyl moiety is suitably a methyl or ethyl group, or a straight or branched propyl, butyl, pentyl or hexyl group. Preferably, $R^1$ and $R^2$ are identical. In a particular embodiment, $R^1$ and $R^2$ are both ethyl.

Where X in the compounds of formula I above represents halogen, this group is suitably fluorine, chlorine, bromine or iodine. Where X represents $C_{1-6}$ alkyl or $C_{1-6}$ alkoxy, the alkyl moiety is suitably a methyl or ethyl group, or a straight or branched propyl, butyl, pentyl or hexyl group. Preferably, X represents hydrogen.

Examples of hindered acyl residues for the substituent $R^3$ in the compounds of formula II above include hindered alkyl groups, and aryl groups. Typical hindered alkyl groups include ethyl, and straight or branched propyl, butyl, pentyl and hexyl groups. A particular hindered alkyl group is represented by the structure $—CHR^aR^b$ in which $R^a$ represents hydrogen, methyl or ethyl and $R^b$ represents methyl or ethyl; in particular wherein $R^a$ represents hydrogen and $R^b$ represents methyl, or $R^a$ and $R^b$ each represents methyl or ethyl. Typical aryl groups include phenyl and naphthyl. Preferably, $R^3$ represents ethyl, isopropyl, t-butyl or pent-3-yl.

By using a hindered vinyl ester of formula II in step (i) of the above-described process, in place of the vinyl acetate derivatives employed in existing methods, significantly higher yields of the desired product of formula III are obtained, with less need to separate unwanted by-products (generally the wrong regioisomer) and lower recovery of unchanged starting material. This surprising effect could not have been predicted from the prior art. As noted above, a detailed study of the cycloaddition reaction between chlorosulphonyl isocyanate and a wide range of vinyl esters is presented in *Justus Liebigs Ann. Chem.* 1974, 539. No suggestion is made therein, however, of the beneficial effect upon the reaction of incorporating a hindered acyl residue into the vinyl ester reactant.

The advantageous effect of employing a hindered vinyl ester in step (i) of the process according to the invention can be optimised still further by judicious choice of reaction conditions. For example, it has been found that higher yields of better quality material are obtainable when the reaction is carried out in a polar organic solvent. This finding accords with the experimental results described in *Justus Liebigs Ann. Chem.*, 1969, 722, 110. Preferably, however, the reaction is carried out in the absence of solvent, since in this way the possibility of reactive by-products and unwanted side-reactions is minimised. Where a polar solvent is nevertheless employed, such solvents suitably include nitromethane and 1,1,1-trichloroethane, preferably nitromethane.

Step (i) of the above process is suitably effected at a temperature of between −10° C. and +40° C., for a time of between 0.5 and 60 hours. Where nitromethane is used as the solvent, the reaction is conveniently carried out at 0° C. for 30 hours. Where the reaction is performed in the absence of solvent, a temperature of 10° C. maintained for 42 hours is generally satisfactory; under these conditions, yields of the desired product of formula III in the region of 90–95% may be expected.

The carboxy-protecting group $R^4$ in the compounds of formulae IV and V above may be any ester residue known from the art to be capable of protecting a carboxy moiety. Suitable carboxy-protecting groups are described in *Protective Groups in Organic Chemistry*, ed. J. F. W. McOmie, Plenum Press, 1973; and T. W. Greene, *Protective Groups in Organic Synthesis*, John Wiley & Sons, 1981. Typical carboxy-protecting groups include t-butyl, benzyl, 4-methoxybenzyl and 4-nitrobenzyl. A particular group $R^4$ is benzyl.

Examples of suitable bases capable of promoting the acyloxy displacement reaction in step (ii) of the process according to the invention include potassium fluoride, sodium carbonate, potassium carbonate, sodium hydroxide, potassium hydroxide and barium hydroxide. A preferred base is barium hydroxide octahydrate. The reaction is conveniently carried out in an inert organic solvent such as toluene or dimethyl acetamide, at a temperature in the region of 40° C. for approximately 3 hours. Where appropriate, further aliquots of the β-lactam derivative of formula III may be added to the reaction mixture as required, in order to ensure that the reaction proceeds to completion.

A means has also been found of enriching the product obtained from step (ii) of the process according to the invention in favour of the desired enantiomeric form. Shifting the stereochemical balance of the intermediates such that the desired enantiomeric form predominates at an early stage is plainly advantageous to the efficiency of the overall process. The stereochemical enrichment procedure comprises mixing the β-lactam derivative III and the phenolic compound IV, as defined above, together with a suitable amount of an asymmetric catalyst, in the presence of a mild base such as anhydrous sodium carbonate; followed by treatment with a base as required by step (ii) of the process according to the invention.

The asymmetric catalyst employed in the above-described stereochemical enrichment procedure advantageously comprises a chiral alkaloid derivative such as cinchonine, cinchonidine or quinine. A particular asymmetric catalyst is cinchonine. The precise nature of the asymmetric catalyst to be employed will ultimately be dependent upon the particular enantiomeric form of the product desired from the reaction. Selection of an appropriate asymmetric catalyst, and ascertainment of the precise amount thereof to be utilised in the procedure, will generally be made by the skilled worker on a trial and error basis.

The asymmetric catalyst/mild base treatment is conveniently effected in an inert organic solvent such as toluene, suitably with heating to between 40° C. and 70° C., preferably to about 55° C., for 2 to 6 days, preferably for approximately 5 days. The product obtained from this treatment can then be treated in situ with base in accordance with step (ii) of the process of the invention, and the subsequent steps of the synthetic sequence performed in the normal way. By utilising the stereochemical enrichment procedure, it has been found that the outcome of the reaction can be influenced to such an extent that enrichment ratios of 3:1 in favour of the desired enantiomer can be obtained, most notably without the necessity for recourse to chromatography.

The stereochemical enrichment procedure described above constitutes a novel process in its own right, and accordingly represents a further feature of the present invention.

Step (iii) of the process according to the invention comprises the removal of the carboxy-protecting group $R^4$. This may suitably be effected using conventional techniques known per se from the art. Where the carboxy-protecting group $R^4$ represents benzyl, a favoured procedure for the removal of this group is transfer hydrogenation. This comprises treating the ester of formula V with a hydrogenation catalyst such as palladium on carbon, in the presence of a hydrogen donor such as cyclohexene. The reaction is suitably carried out in a solvent such as industrial methylated spirit (IMS), advantageously at the reflux temperature of the solvent employed. The time taken for complete reaction will vary depending inter alia upon the amount of hydrogenation catalyst in the reaction mixture. Where a 10% palladium on carbon catalyst is employed, this catalyst will advantageously be present in an amount of from 5% to 10% by weight of the ester of formula V, in which case a reaction time of between 1 and 6 hours will be required.

By "appropriate chiral amine" in step (iv) of the process according to the invention is meant any chiral amine capable of preferentially forming a crystalline salt thereof with the desired enantiomer of the β-lactam carboxylic acid of formula I. A particular chiral amine in this regard is α-methylbenzylamine. The decision as to which optical isomer of the chiral amine to use will depend upon the chirality of the desired enantiomer of the β-lactam carboxylic acid of formula I, and will in general be made by the skilled worker on the basis of trial and error.

For instance, where n is 1, $R^1$ and $R^2$ are both ethyl, and X is hydrogen, a preferred chiral amine is (S)-(−)-α-methylbenzylamine; this chiral amine gives rise, as indicated in the accompanying Examples, to the (S)-(−)-α-methylbenzylammonium salt of the 4(S) enantiomer of the β-lactam carboxylic acid as represented by formula IB:

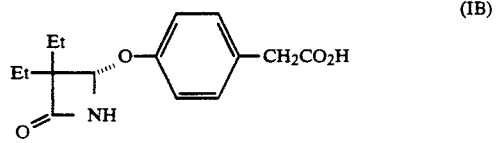
(IB)

Step (iv) of the process according to the invention is conveniently carried out by treating the mixture of stereoisomers of formula IA with the chiral amine in an inert organic solvent such as ethyl acetate, and stirring at room temperature for 12 to 24 hours.

Once the crystalline salt has been filtered off, the desired enantiomer of the β-lactam carboxylic acid derivative of formula I can be regenerated by acidification, as specified in step (vi) of the process according to the invention. This may be conveniently effected by dissolving the salt in an inert organic solvent such as ethyl acetate, and treating with a dilute aqueous solution of a mineral acid. Suitable mineral acids include hydrochloric acid and sulphuric acid, preferably hydrochloric acid.

If desired, the resolved 4-aryloxyazetidin-2-one derivative of formula I obtained at the end of the synthetic sequence may be modified, for example by attachment of a carboxy-protecting group $R^4$ as defined above to the carboxy moiety thereof, using methods known per se from the art.

The individual enantiomers of the resolved 4-aryloxyazetidin-2-one derivatives of formula I as defined above are novel compounds, and accordingly constitute a further feature of the present invention. In particular, the present invention provides that enantiomer of the compounds of formula I as defined above which possesses the (S) configuration at the 4-position of the azetidinone ring.

The intermediates of formulae III, V and IA above may be isolated as such after steps (i), (ii) and (iii) respectively of the process according to the invention, in which case steps (i) to (iv) may be carried out independently; or the procedures of any or all of steps (ii) to (iv) may be performed in situ on the reaction mixture resulting from each preceding step. From the point of view of the yield obtained from the overall process of the invention, it is preferred that the procedure of each of steps (ii) to (iv) is performed in situ on the reaction mixture resulting from the preceding step.

Where they are not commercially available, the reagents of formulae II and IV above may be prepared by the methods described in the accompanying Examples, or by methods analogous thereto which will be readily apparent to those skilled in the art.

Since the intermediates III and V in the process according to the invention generally consist of a mixture of desired and unwanted enantiomeric forms, it follows that a good deal of the material would be wasted upon resolution of the mixture of stereoisomers of formula IA unless a method were available for racemising the unwanted isomer of formula I remaining after the resolution procedure. We have now found that such a racemisation can be achieved efficiently, thereby benefiting the overall process considerably from an economic viewpoint.

In a further aspect, therefore, the present invention provides a process for the racemisation of the unwanted enantiomer of a compound of formula I as defined above, which process comprises the following steps:

(a) attachment of a carboxy-protecting group $R^4$ to the carboxy moiety of the unwanted enantiomer of the compound of formula I;

(b) treatment of the carboxy-protected compound thereby obtained with a catalytic amount of a tertiary organic base, to obtain a compound of formula V as defined above in racemic form; and (c) removal of the carboxy-protecting group $R^4$ from the racemate of formula V thereby obtained, to obtain a compound of formula IA as defined above in racemic form.

It will be appreciated that step (c) in the above-described racemisation process corresponds to step (iii) of the process according to the invention. Thus, once the racemate of formula IA is obtained from step (c) of the racemisation process it can, if desired, be resolved following steps (iv) to (vi) of the process according to the invention in the normal way.

Attachment and removal of the carboxy-protecting group $R^4$ according to steps (a) and (c) respectively of the above process can be effected by conventional procedures known per se from the art, and discussed previously.

Examples of tertiary organic bases of use in step (b) of the above process suitably include 1,8-diazabicyclo[5.4.0]undec-7-ene (DBU) and 1,5-diazabicyclo[4.3.0]non-5-ene (DBN), preferably DBU. The reaction is conveniently effected by treating the carboxy-protected substrate with 0.01 to 0.1 equivalents, preferably 0.05 equivalents, of the tertiary organic base in an inert organic solvent such as toluene. The reaction mixture is advantageously heated at the reflux temperature of the solvent employed for 0.5 to 4 hours, as required for complete racemisation.

The following non-limiting Examples are intended to illustrate the present invention.

EXAMPLE 1

Step A: 1-Propionyloxy-2-ethyl-1-butene (II, $R^1=R^2=R^3=Et$)

A 30 gallon stainless steel reaction vessel was charged sequentially with triethylamine (12.8 l), propionic anhydride (14.48 l), 4-dimethylaminopyridine (94 g) and 2-ethylbutyraldehyde (7.5 l, assay 92%, obtainable from Aldrich Chemical Co. Ltd., Gillingham, England). The mixture was stirred and heated under gentle reflux (120°–135° C.) for 5 hours in a nitrogen atmosphere. The reaction mixture was assayed by the partitioning of a sample between hexane and water. GC analysis of the hexane layer [CP SIL S CB column, injection temp.=200° C., detection temp.=300° C., conditions: 35° C. (3 minutes), then 10° C. min$^{-1}$ up to 280° C. (2 minutes)] showed <2% starting aldehyde, 80% product, 3.8% diester and 10.9% anhydride.

The reaction mixture was cooled to 70° C. and water (13.5 l) added. The initial addition rate was slow to accommodate an exotherm (approx. 20° C. rise). On complete addition, the mixture was heated at reflux for 45 minutes. The reaction was cooled to room temperature and hexane (7.5 l) added. The aqueous layer was separated and re-extracted with hexane (5 l). The organic extracts were combined and washed with saturated NaHCO$_3$ solution (2×7.5 l) and evaporated in vacuo at 40° C. The residue (approx. 10 kg) was fractionally distilled, b.p. 75°–80° C. (30–40 mmHg) to give the product as a mobile liquid. Yield: 7.712 kg, 88%. GC profile 98.7%.

Step B: 4-Propionyloxy-3,3-diethylazetidin-2-one (III, $R^1=R^2=R^3=Et$)

The vinyl ester (II, $R^1=R^2=R^3=Et$, 2.5 kg) was dissolved in nitromethane (1.25 l) and the solution allowed to cool to −2° C. overnight in an IMS/H$_2$O bath using a cryocool. Chlorosulphonyl isocyanate (obtainable from Lonza AG, Basle, Switzerland; 2.1 l) was added over 30 minutes maintaining the temperature at <6° C. On complete addition, the yellow solution was cooled to 0° C. and stored under a N$_2$ atmosphere for 30 hours. The reaction mixture was diluted with diethyl ether (4 l) and charged to the addition funnel of a 20 gallon glass-lined vessel which itself contained a mixture of water (70 l), sodium sulphate (7.5 kg) and sodium bicarbonate (12.5 kg) at 5° C. A further portion of diethyl ether (2.5 l) was used to rinse the 10 l flask containing the reaction mixture into the addition funnel. The reaction mixture was slowly added to the quench mixture over 30 minutes (maintaining the temperature at <5° C.). The cooling vessel was removed and the contents allowed to warm to 15° C. over 1 hour. Gas evolution by this time had ceased. The reaction mixture was filtered through an Estrella filter into a 100 gallon glass reactor. The 20 gallon glass vessel was rinsed with water (10 l) and t-butylmethyl ether (15 l) and this was used to rinse the filter and the lines. The lower aqueous layer was separated and re-extracted with t-butylmethyl ether (15 l). The organic extracts were combined, washed with saturated brine solution (20 l) and dried (Na$_2$SO$_4$), and the solvents were removed in vacuo (maintaining the temperature at <35° C.) to give the product as a yellow oil. Yield: 2.64 kg, 83%. GC/MS showed 90.8% product (III, $R^1=R^2=R^3=Et$), 6.2% regioisomeric by-product and 1.4% starting ester (II, $R^1=R^2=R^3=Et$).

Step C: 4-Hydroxyphenylacetic acid benzyl ester (IV, n=1, $R^4=CH_2Ph$, X=H)

A 20 gallon glass-lined vessel was charged with N,N-dimethylformamide (15.9 l) and 4-hydroxyphenylacetic acid (3.969 kg, 26.09 moles). When solution was obtained, lithium carbonate (2.12 kg, 28.7 moles, 1.1 equivs.) was added in one portion and the resulting mixture stirred at room temperature for 10 minutes. Benzyl bromide (3.723 l, 31.3 moles, 1.2 equivs.) was added in one portion and the mixture heated to 100° C. (internal temperature) and held for 3 hours, when LC (40/60, 0.0025 M H$_3$PO$_4$/CH$_3$CN, 220 nm, 1.5 mlmin$^{-1}$, Hypersil column) showed approx. 5% starting acid remained. The reaction was cooled to approx. 60° C. and 2N aqueous HCl solution (20 l) was added and the solution extracted with ethyl acetate (2×10 l). The combined organic extracts were washed with saturated NaHCO$_3$ solution (16 l) and water (3×16 l). Emulsions were encountered during water washing, which could be broken by the addition of toluene (20 l total). The ethyl acetate was removed by distillation until the level of residual ethyl acetate was <0.3% [additional toluene (5 l) was added during distillation]. The volume of the mixture was adjusted to approx. 16 l (by further distillation) and allowed to cool to room temperature when crystallisation occurred. The slurry was diluted by the addition of hexane (20 l) and aged at ambient temperature overnight. The slurry was cooled to 0° C., held for 1 hour and the product filtered, washed with a cold (0° C.) 1:1 toluene/hexane mixture (4 l) and dried in vacuo at 50° C. to give the product as a white solid. Yield: 5.283 kg, 83%. LC/GC>98%. NMR confirmed structure; only trace impurities noted.

Step D: Benzyl 4-((3,3-diethyl-4-oxo-2-azetidinyl)-oxy)benzeneacetate (V, N=1, $R^1=R^2=Et$, $R^4=CH_2Ph$, X=H)

A 20 gallon glass-lined vessel was charged with toluene (65 l) and the ester (IV, n=1, $R^4=CH_2Ph$, X=H, 2.68 kg, 11.07 mole) and heated at 40° C. until a solution was obtained. Barium hydroxide.8H$_2$O (4.20 kg, 13.31 mole) was added in one portion and the resulting slurry stirred at 40° C. for 10 minutes. A solution of the β-lactam (III, R$^1$=R$^2$=R$^3$=Et, 2.57 kg, 11.73 mole based on 90.8% assay) in toluene (10 l) was added over 15 minutes to the resulting thick slurry at 40° C. (no exotherm observed). After 1.5 hours, TLC (30% ethyl acetate in hexane) showed a trace of starting phenol and so a second portion of β-lactam (III, R$^1$=R$^2$=R$^3$=Et, 70 g) was added. After 30 minutes, TLC showed complete reaction. The mixture was cooled to 15° C. and 2N HCl solution (30 l) was added. The aqueous lower layer was separated and the organic layer washed with saturated NaHCO$_3$ solution (2×30 l) and saturated brine solution (20 l). The reaction mixture was concentrated in vacuo (maintaining the temperature at <45° C.) to give the product as a viscous yellow oil. Yield: 3.805 kg, 93.6%. LC (40/60, 0.0025M H$_3$PO$_4$/CH$_3$CN, 220 nm, 1.5 mlmin$^{-1}$, Hypersil column) showed 94.2% product and 1.4% toluene. NMR indicated that the product was approx. 95% pure.

Step E:
4-((3,3-Diethyl-4-oxo-2-azetidinyl)oxy)-benzeneacetic acid (IA, n=1, R$^1$=R$^2$=Et, X=H)

The benzyl ester (V, n=1, R$^1$=R$^2$=Et, R$^4$=CH$_2$Ph, X=H, 5.24 kg, 14.26 moles) was dissolved in IMS (34.5 l) and cyclohexene (10.5 l) containing 10% Pd/C (524 g). The mixture was stirred and heated under reflux in a 30 gallon stainless steel vessel. After 3 hours at reflux, LC (50/50, 0.0025M H$_3$PO$_4$/CH$_3$CN, 220 nm, 1.5 mlmin$^{-1}$, Hypersil column) showed only a trace of starting ester. The batch was cooled to 25° C. and filtered through Whatman GF/A paper to remove the catalyst (slow). The pad was rinsed with ethyl acetate and the washings and filtrate combined and the solvent removed in vacuo (maintaining the temperature at <40° C.) to give a viscous oil. The oil was partitioned between 10% aqueous potassium carbonate solution (6 l) and ethyl acetate (7 l). The lower aqueous layer was separated and re-extracted with ethyl acetate (7 l). The aqueous solution was acidified with 5N HCl solution (approx. 4.8 l) and extracted with ethyl acetate (10 l). The lower aqueous layer was separated and re-extracted with ethyl acetate (7 l). The organic extracts were combined, washed with water (5 l), dried (Na$_2$SO$_4$) and evaporated in vacuo (maintaining the temperature at <40° C.) to give the product as a viscous oil which solidified in the cold room. Yield: 3.55 kg, 90%. NMR confirmed identity of product; only very minor impurities noted.

Step F: Resolution of β-lactam acid (IA, n=1, R$^1$=R$^2$=Et, X=H) via (R)-(+)- and (S)-(−)-α-methylbenzylamine salts Acid (IA, n=1, R$^1$=R$^2$=Et, 253.3 g, 0.91 moles) was dissolved in ethyl acetate (1.27 l) and treated with (R)-(+)-α-methylbenzylamine (117.7 ml, 110.6 g, 0.91 moles) and the solution seeded with pure (>97:3) salt. The resulting mixture was stirred at room temperature overnight and then chilled at 0°-5° C. for 1 hour, filtered, washed with a little cold ethyl acetate and dried in air. Yield: 124 g. This material was swished in ethyl acetate (1.2 l) at 60° C. for 1 hour. The mixture was cooled at 0°-5° C. for 1.5 hours, filtered, washed with a little fresh solvent and dried in vacuo at 40° C. to give the unwanted (R)-(+)-α-methylbenzylamine (α-MBA) salt. Yield: 91.44 g, 25%. NMR showed the ratio of diastereomers to be 95:5. The filtrates of the original salt formation and the swish were combined and washed with 2N HCl solution (3×350 ml) and then brine solution (350 ml). The organic layer was dried (Na$_2$SO$_4$) and evaporated to give a viscous oil (187 g). This oil was dissolved in ethyl acetate (935 ml) and treated with (S)-(−)-α-MBA as described above to give crude wanted (S)-(−)-α-MBA salt, yield: 175 g. This was swished in ethyl acetate as previously described to give pure (S)-(−)-α-MBA salt (119.84 g) in 33% yield; m.p. 129°-130° C. NMR diastereomeric ratio 98:2. The salt formation and swish liquors were treated as described above with dilute HCl solution to regenerate the free acid (IA, n=1, R$^1$=R$^2$=Et, X=H) and hence a second crop of (R)-(+)-α-MBA salt (49.68 g) was obtained in 13.7% yield, i.e. total of unwanted (R)-(+)-α-MBA salt =141.2 g, 38.6%. These liquors were also treated similarly and in an exactly analogous manner a second crop of (S)-(−)-α-MBA salt (18.8 g) was obtained in 5.2% yield, i.e. total of wanted (S)-(−)-α-MBA salt=13.64 g, 38%, i.e. 76% of the available isomer.

The bulk acid (IA, n=1, R$^1$=R$^2$=Et, X=H, 8.03 kg total) was treated similarly to give cure (S)-(−)-α-MBA salt (4.39 kg, 38%) (isomer ratio >97:3).

Step G: Resolved benzyl 4-((3,3-diethyl-4-oxo-2-azetidinyl)oxy)benzeneacetate

The (S)-(−)-α-methylbenzylamine salt of the resolved acid (IB, 3.35 kg, 8.41 moles) was partitioned between ethyl acetate (21 l) and 2N aqueous HCl solution (4.2 l) with stirring for 15 minutes. The lower aqueous layer was separated and the organic layer washed with 2N aqueous HCl solution (2×4.2 l) and then water (2×5 l). The organic solution was dried (Na$_2$SO$_4$) and evaporated to give the resolved acid (IB, 2.36 kg) in quantitative yield.

The oil was dissolved in DMF (11.8 l) (KF: 0.015% H$_2$O) and stirred overnight with ground potassium Carbonate (698 g, 5.05 moles, ≡1.2 equivs. of base) and benzyl bromide (1.02 l, 1.47 kg, 8.57 moles, 1.02 equivs.) at room temperature. LC (50/50, 0.0025M H$_3$PO$_4$/CH$_3$CN, 220 nm, 1.5 mlmin$^{-1}$, Hypersil column) showed trace of acid (IB) at retention time 2.93 minutes, benzyl bromide at retention time 7.50 minutes and resolved benzyl 4-((3,3-diethyl-4-oxo-2-azetidinyl)oxy)-benzeneacetate at retention time 14 minutes. The reaction was quenched by addition of water (26 l) and then extracted with t-butylmethyl ether (14 l). The lower aqueous layer was separated and re-extracted with t-butylmethyl ether (14 l). The organic layers were combined and washed with water (2×10 l), dried (Na$_2$SO$_4$) and evaporated to give the product as a viscous oil.

Yield: 2.87 kg, 93%. [α]$_D$=−60.8° (C=1.0 in 1,1,1-trichloroethane).

EXAMPLE 2

The (S)-(−)-α-methylbenzylamine salt of the β-lactam acid IB

A mixture of the phenol (IV, n=1, R$^4$=CH$_2$Ph, X=H, 11 g, 0.045 mole), the β-lactam (III, R$^1$=R$^2$=R$^3$=Et, 12 g at approx. 75% assay ≡9 g, 0.045 mole), ground anhydrous Na$_2$CO$_3$ (4.75 g) and cinchonine (1.36 g) in toluene (340 ml) was stirred and heated at 55° C. for 120 hours under a nitrogen atmosphere. LC (0.0025M H$_3$PO$_4$/CH$_3$CN, 40/60, 220 nm, 1.5 mlmin$^{-1}$, Hypersil column) showed the ratio of (IV, n=1, $R^4$=CH$_2$Ph, X=H): (V, n=1, $R^1$=$R^2$=Et, $R^4$=CH$_2$Ph, X=H) to be 31:69. The reaction mixture was cooled to room temperature and barium hydroxide.8H$_2$O (4.44 g, 0.014 mole) and β-lactam (III, $R^1$=$R^2$=$R^3$=Et, 3.74 g at 75% assay, 0.014 mole) added. The reaction mixture was warmed to 40° C. After 3 hours, LC (as above) showed 88% product (V, n=1, $R^1$=$R^2$=Et, $R^4$=CH$_2$Ph, X=H) and 12% phenol (IV, n =1, $R^4$=CH$_2$Ph, X=H). The reaction was worked up by partitioning between ether (110 ml) and 2N HCl (110 ml). The organic layer was washed with another portion of 2N HCl (110 ml) and then water (110 ml), followed by saturated NaHCO$_3$ solution (2×110 ml), dried (Na$_2$SO$_4$) and evaporated.

The mixture was dissolved in toluene (400 ml) and barium hydroxide.8H$_2$O (1.72 g) and β-lactam (III, $R^1$=$R^2$=$R^3$=Et, 1.45 g at 75% assay) added. The resulting mixture was heated to 40° C. and held for 3 hours, during which time the reaction went to completion. The reaction mixture was cooled to room temperature and worked-up as described above to give the ester (V, n=1, $R^1$=$R^2$=Et, $R^4$=CH$_2$Ph, X=H, 23 g) as a viscous oil.

The oil (23 g) was dissolved in IMS (149 ml) and cyclohexene (46 ml). 10% Pd/C (2.3 g) was added and the mixture stirred and heated under reflux for 3 hours. The reaction was cooled and filtered through Whatman GF/A paper to remove the catalyst. The solvent was removed in vacuo to give the crude acid (IA, n=1, $R^1$=$R^2$=Et, X=H) as a gum. The product was partitioned between ethyl acetate (30 ml) and 10% aqueous K$_2$CO$_3$ solution (65 ml). The organic layer was washed with a second portion of 10% aqueous K$_2$CO$_3$ solution (35 ml). The aqueous solutions were combined and washed with ethyl acetate (30 ml) and then acidified with 5N aqueous HCl solution (30 ml) and the liberated acid extracted into ethyl acetate (40 ml). The aqueous layer was re-extracted with ethyl acetate (30 ml) and the combined organic extracts washed with water (2×30 ml), dried (Na$_2$SO$_4$) and evaporated to give the acid (IA, n=1, $R^1$=$R^2$=Et, X=H). The acid product was dissolved in ethyl acetate (63 ml) and (S)-(−)-α-methylbenzylamine (5.5 g, 0.045 mole) was added. The solution was seeded and the resulting slurry stirred at room temperature overnight. Next day, the slurry was cooled to 0° C., held for 1 hour and then filtered, washed with a little cold ethyl acetate and then ether and dried. Yield: 12.27 g, 68%. NMR showed an approx. 8:1 mixture of enantiomers.

The solid (12.27 g) was swished in hot (60° C.) ethyl acetate (120 ml) for 1 hour, stirred at room temperature for 1 hour, cooled to 0° C. and held for 1 hour, and then filtered, washed with a little ethyl acetate and dried. Yield: 10.1 g, 82% recovery. NMR showed a 98:2 mixture of diastereomeric salts.

The liquors from the above swish and the original salt formation were combined and washed with 2N aqueous HCl (3×20 ml) and then water (20 ml), dried (Na$_2$SO$_4$) and evaporated to give the free acid (IB, 5.83 g). In an analogous manner as described above, this was converted into the (R)-(+)-α-methylbenzylamine salt which was swished and the combined filtrate liquors treated with 2N aqueous HCl to give the free acid IB which was converted into the (S)-(−)-α-methylbenzylamine salt again which was swished to give a second crop of 99:1 salt (1 g).

Total amount of swished resolved (98:2) (S)-(−)-α-methylbenzylamine salt of the acid IB=11.1 g, 61% yield from phenol (IV, n=1, $R^4$=CH$_2$Ph, X=H, 11 g).

EXAMPLE 3

Racemisation of the unwanted isomer of β-lactam ester (V, n=1, $R^1$=$R^2$=Et, $R^4$=CH$_2$Ph, X=H)

Chiral (unwanted) β-lactam ester (V, n=1, $R^1$=$R^2$=Et, $R^4$=CH$_2$Ph, X=H, 10 g) in toluene (100 ml) containing DBU (0.2 ml, 0.05 equivs.) was heated under reflux for 40 minutes and then cooled to 40° C. LC showed approx. 12% of the phenol (IV, n=1, $R^2$=CH$_2$Ph, X=H) generated and so barium hydroxide.8H$_2$O (1.2 g) was added and the mixture stirred for 5 minutes. β-Lactam (III, $R^1$=$R^2$=$R^3$=Et, 0.76 g, 85% assay = 0.65 g) was added and the resulting mixture aged at 40°–45° C. for 2.5 hours. The reaction mixture was cooled to room temperature, diluted with ether (100 ml) and washed with 2N aqueous HCl solution (2×50 ml), then saturated with NaHCO$_3$ solution (2×50 ml), dried (Na$_2$SO$_4$) and evaporated to give the product as an oil. Yield: 10.41 g, 104% (but contains 6% by weight of toluene). LC approx. 90%.

EXAMPLE 4

Step A: 2-Ethyl-1-(2-ethylbutyryloxy)-1-butene (II, $R^1$=$R^2$=Et, $R^3$=CHEt$_2$)

A 2 liter 3-necked flask was charged with 2-ethylbutyric anhydride (381 ml), 2-ethylbutyraldehyde (200 ml), triethylamine (230 ml) and 4-dimethylaminopyridine (18.3 g). The mixture was warmed slowly to approximately 30° C. to obtain homogeneous solution, then heated at gentle reflux (120°–150° C.). The reaction progress was followed by capillary GC analysis [D.B.S. column, 15m, injection temperature=250° C., detection temperature=300° C., conditions: 30° C. (2 minutes), then 10° C. min$^{-1}$ up to 300° C., flow 2 ml/minute] showed <1% aldehyde after 6 hours. The reaction mixture was cooled to 90° C. and water (400 ml) added over 5 minutes. The resultant mixture was warmed to reflux for 1 hour (to hydrolyse excess anhydride). The mixture was cooled to 25° C., then water (200 ml) and hexane/ethyl acetate (3:1, 200 ml) were added. The lower aqueous layer was separated. The organic layer was washed with 2N hydrochloric acid (2×100 ml), saturated NaHCO$_3$ solution (2×100 ml) and dried (Na$_2$SO$_4$). The solution was evaporated in vacuo and the residue distilled, b.p. 58°–64° C. (1 mmHg), to give the product as a liquid. Yield: 274 g, 92%. GC Assay 97.5%.

Step B: 3,3-diethyl-4-(2-ethylbutyryloxy)-2-azetidinone (III, $R^1$=$R^2$=Et, $R^3$=CHEt$_2$)

The vinyl ester (II, $R^1$=$R^2$=Et, $R^3$=CHEt$_2$, 50.0 g, 0.246 mole) in a 250 ml flask was cooled to 10° C., with stirring under a N$_2$ atmosphere. Chlorosulphonyl isocyanate (33 ml, 0.369 mole) was added dropwise over 15 minutes (no apparent exotherm), maintaining reaction temperature at 10° C.±1° C. for 42 hours. The reaction mixture was diluted with toluene (100 ml) and added dropwise over 1 hour to a slurry of sodium bicarbonate (196 g) and sodium sulphite (117 g) in water (1100 ml) at 20° C. (exotherm to approximately 28° C. and effervescence). On complete addition the slurry was stirred at approximately 25° C. for 4 hours (slow evolution of CO$_2$). Ethyl acetate (100 ml) and water (approximately 1000 ml) were added to dissolve the inorganic salts. The aqueous layer was separated and extracted with ethyl acetate (200 ml). The combined organic layer was washed with brine (80 ml) and dried ($Na_2SO_4$). The solution was evaporated in vacuo to give the product as a colourless oil. Yield 57.0 g, 96%. NMR showed approximately 3% regioisomeric by-product.

Step C: Benzyl 4-((3,3-diethyl-4-oxo-2-azetindinyl)-oxy)benzeneacetate (V, n=1, $R^1=R^2=Et$, $R^4CH_2Ph$, X=H)

To a solution of benzyl 4-hydroxyphenylacetate (IV, n=1, $R^4=CH_2Ph$, X=H, 2.6g, 11 mmol) in N,N-dimethylformamide (20 ml) was added water (2.8 ml) and milled anhydrous potassium carbonate (4.5 g, 32 mmol). The mixture was stirred at 35° C. and the azetidinone (III, $R^1=R^2=Et$, $R^3=CHEt_2$, 3.4 g, 93% assay, 13 mmol) in N,N-dimethylformamide (4 ml) added. The mixture was stirred at 30° C. for 1 hour and then cooled to 20° C. 2N aqueous HCl solution (15 ml) was added and the mixture extracted with ethyl acetate (2×20 ml). The organic solution was washed with saturated aqueous $NaHCO_3$ solution (15 ml), water (10 ml) and saturated brine (10 ml). The solution was evaporated in vacuo to give the benzyl ester (V, n=1, $R^1=R^2=Et$, $R^4=CH_2Ph$, X=H) as a yellow oil. Assay yield 3.8 g (94%).

What is claimed is:

1. A process for the preparation of the 4(S) enantiomer of a 4-aryloxyazetidin-2-one derivative of the formula I:

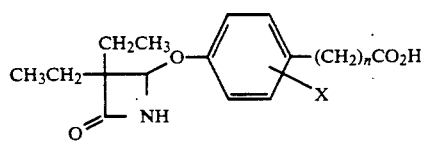

wherein
n is zero or a positive whole integer from 1 to 6; and
X is selected from the group consisting of hydrogen, halogen, $C_{1-6}$ alkyl and $C_{1-6}$ alkoxy; which process comprises the following steps:
(i) reaction of a compound of formula II:

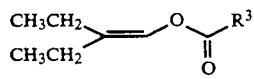

wherein
$R^3$ represents a hindered acyl residue, $-CHR^aR^b$, in which $R^a$ is selected from the group consisting of hydrogen, methyl and ethyl and $R^6$ represents methyl or ethyl; with chlorosulphonyl isocyanate, to obtain a β-lactam derivative of formula III:

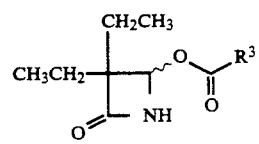

wherein
$R^3$ is as defined above, and the wavy line indicates that a mixture of enantiomers at the position indicated is obtained:

(ii) reaction of the β-lactam derivative of formula III with a phenolic compound of formula IV:

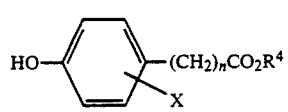

wherein
n and X are as defined above, and
$R^4$ represents a carboxy-protecting group; in the presence of a base, to obtain a compound of formula V:

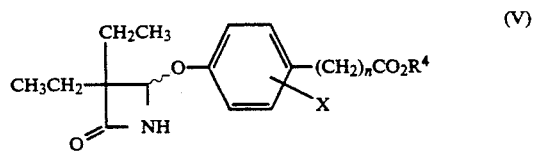

wherein
n, $R^4$, X and the wavy line are as defined above;
(iii) removal of the carboxy-protecting group $R^4$ from the compound of formula V thereby obtained, to obtain a compound of formula IA:

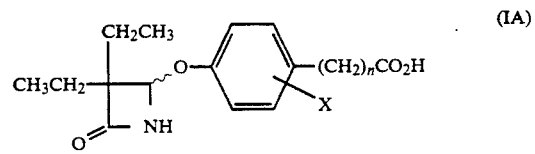

wherein n, X and the wavy line are as defined above;
(iv) treatment of the compound of formula IA thereby obtained with an approximately equimolar amount of a chiral amine, to obtain the corresponding chiral amine salt of the 4(S) enantiomer of the β-lactam carboxylic acid of formula I;
(v) filtering the reaction mixture; and
(vi) acidifying the solid salt thereby obtained in order to regenerate the desired 4(S) enantiomer of the 4-aryloxyacetidin-2-one derivative of formula I in substantially optically-pure form.

2. A process according to claim 1 wherein, in step (iv), the chiral amine utilised is α-methylbenzylamine.

3. A process according to claim 1 wherein, in step (i), the reaction is carried out in the absence of solvent.

4. A process according to claim 1 wherein, in step (ii), the base utilised is selected from the group consisting of potassium fluoride, sodium carbonate, potassium carbonate, sodium hydroxide, potassium hydroxide and barium hydroxide.

5. A process according to claim 1 wherein the product obtained from step (ii) is enriched in favour of the desired enantiomeric form by mixing the β-lactam derivative III and the phenolic compound IV, as defined in claim 1, together with a suitable amount of an asymmetric catalyst, in the presence of a mild base; prior to treatment with a base as required by step (ii) of the process according to claim 1.

6. A process according to claim 5 wherein the asymmetric catalyst utilised is a chiral alkaloid derivative selected from cinchonine, cinchonidine and quinine.

* * * * *